United States Patent [19]

Billig et al.

[11] 4,348,539
[45] Sep. 7, 1982

[54] HETERONUCLEAR-BRIDGED RHODIUM CLUSTERS

[75] Inventors: Ernst Billig; Jackie D. Jamerson, both of Charleston, W. Va.; Roy L. Pruett, New Providence, N.J.

[73] Assignee: Union Carbide Corporation, Danbury, Conn.

[21] Appl. No.: 260,920

[22] Filed: May 6, 1981

Related U.S. Application Data

[62] Division of Ser. No. 90,140, Nov. 1, 1979, Pat. No. 4,288,380.

[51] Int. Cl.$^3$ .................................................. C07C 45/50
[52] U.S. Cl. ........................... 568/454; 252/431 N; 252/431 P; 260/429 K; 568/909
[58] Field of Search ............... 568/454, 909; 252/431 P, 431 N; 260/429 R

[56] References Cited

U.S. PATENT DOCUMENTS

| | | | |
|---|---|---|---|
| 3,527,809 | 9/1970 | Pruett et al. | 260/604 HF |
| 3,833,634 | 9/1974 | Pruett et al. | 252/431 R X |
| 3,917,661 | 11/1975 | Pruett | 260/410 |
| 3,940,432 | 2/1976 | Walker et al. | 252/431 N X |
| 3,944,588 | 3/1976 | Kaplan | 260/449 L |
| 3,948,965 | 4/1976 | Cowse | 252/431 N X |
| 3,952,039 | 4/1976 | Walker et al. | 252/431 N X |
| 3,957,857 | 5/1976 | Pruett | 260/449 |
| 3,968,136 | 7/1976 | Walker et al. | 252/431 N X |
| 3,989,799 | 11/1976 | Brown | 260/429 R X |
| 4,055,582 | 10/1977 | Fahey | 260/439 R |
| 4,111,972 | 9/1978 | Fahey et al. | 260/439 R |
| 4,111,975 | 9/1978 | Cawse et al. | 252/431 R X |
| 4,115,433 | 9/1978 | Cosby | 260/449 L |
| 4,118,408 | 10/1978 | Fahey et al. | 260/439 R |
| 4,120,907 | 10/1978 | Fahey et al. | 260/666 B |
| 4,180,517 | 12/1979 | Vidal et al. | 260/449 L |
| 4,247,486 | 1/1981 | Brewester et al. | 568/454 |
| 4,259,530 | 3/1981 | Matsushima et al. | 568/454 |
| 4,260,828 | 4/1981 | Morrell et al. | 568/454 |
| 4,262,142 | 4/1981 | Sherman et al. | 568/454 |
| 4,277,627 | 7/1981 | Bryant et al. | 568/454 |
| 4,288,380 | 9/1981 | Billig et al. | 252/431 P |
| 4,288,634 | 9/1981 | Sakakibara et al. | 568/454 |

OTHER PUBLICATIONS

Ryan et al., "J. Am. Chem. Soc.", vol. 99, pp. 1986–1988 (1977).
"Plat. Metals Review", vol. 19, pp. 88–92 (1975) Thompson.
Gregorio et al., "Proceedings Symposium on Rhodium in Homogeneous Catalysis," Vepzprem, Hungary, Sep. 11–13 (1978), pp. 121–127.
Kreter et al., "11th Central Regional Amer. Chem. Soc. Meeting" Paper Inorg. #4 (May 7–9, 1979).

*Primary Examiner*—Werren B. Lone
*Attorney, Agent, or Firm*—Reynold J. Finnegan

[57] ABSTRACT

Heteronuclear-bridged rhodium clusters useful as catalysts in the hydroformylation of olefins.

11 Claims, No Drawings

HETERONUCLEAR-BRIDGED RHODIUM CLUSTERS

This application is a division of our prior U.S. application: Ser. No. 090,140, filing date Nov. 1, 1979, now U.S. Pat. No. 4,288,380.

FIELD OF THE INVENTION

This invention relates to novel heteronuclear-bridged rhodium clusters as well as to improved process for preparing aldehydes by the hydroformylation of an olefin in the presence of a rhodium catalyst, the improvement comprising employing as the catalyst for said process the novel heteronuclear-bridged rhodium clusters of this invention.

BACKGROUND OF THE INVENTION

Low pressure oxo hydroformylation of an olefin with carbon monoxide and hydrogen in the presence of a rhodium complex catalyst to produce aldehydes is now well known in the art.

For instance, U.S. Pat. No. 3,527,809, the entire disclosure of which is incorporated herein by reference thereto, discloses a hydroformylation process where olefins are hydroformylated with carbon monoxide and hydrogen in the presence of a rhodium complex catalyst and free triarylphosphine to produce aldehydes in high yields at low temperatures and pressures, where the normal to iso-(or branch chain) aldehyde isomer ratio of product aldehydes is high.

It is also known that, under hydroformylation conditions, some of the product aldehydes may condense to form by-product, high boiling aldehyde condensation products such as aldehyde dimers or trimers. Commonly-assigned U.S. Pat. No. 4,148,830, the entire disclosure of which is incorporated herein by reference thereto, disclosed the use of these high boiling liquid aldehyde condensation products as a reaction solvent for the catalyst.

In addition commonly-assigned copending U.S. Application Ser. No. 776,934, filed Mar. 11, 1977, now U.S. Pat. No. 4,247,486 (Belgium Pat. No. 853,377), the entire disclosure of which is incorporated herein by reference thereto, discloses a liquid phase hydroformylation reaction using a rhodium complex catalyst, wherein the aldehyde reaction products and some of their higher boiling condensation products are removed in vapor form from the catalyst containing liquid body (or solution) at the reaction temperature and pressure. The aldehyde reaction products and the condensation products are condensed out of the off gas from the reaction vessel in a product recovery zone and the unreacted starting materials (e.g., carbon monoxide, hydrogen and/or alpha-olefin) in the vapor phase from the product recovery zone are recycled to the reaction zone. Furthermore, by recycling gas from the product recovery zone coupled with make-up starting materials to the reaction zone in sufficient amounts, it is possible, using a $C_2$ to $C_5$ olefin as the alpha-olefin starting material, to achieve a mass balance in the liquid body in the reactor and thereby remove from the reaction zone at a rate at least as great as their rate of formation essentially all the higher boiling condensation products resulting from self-condensation of the aldehyde product.

It is also known in the prior art that even in the absence of intrinsic poisons there may be deactivation of rhodium hydroformylation catalysts under hydroformylation of rhodium hydroformylation catalysts under hydroformylation conditions. Copending, commonly-assigned U.S. patent application Ser. No. 762,336 filed Jan. 25, 1977, abandoned in favor of continuation U.S. Application Ser. No. 151,293, now U.S. Pat. No. 4,277,627, (Belgium Pat. No. 863,268), the entire disclosure of which is incorporated herein by reference thereto, indicates that the deactivation of rhodium hydroformylation catalysts under hydroformylation conditions in the substantial absence of extrinsic poisons is due to the combination of the effects of temperature, phosphine ligand:rhodium mole ratio, and the partial pressures of hydrogen and carbon monoxide and is termed an intrinsic deactivation. It is further disclosed therein that this instrinsic deactivation can be reduced or substantially prevented by establishing and controlling and correlating the hydroformylation reaction conditions to a low temperature, low carbon monoxide partial pressure and high free triarylphosphine ligand-:catalytically active rhodium mole ratio.

It has also been observed that the presence of an alkyldiarylphosphine (for example, propyldiphenylphosphine or ethyldiphenylphosphine) in the rhodium-catalyzed hydroformylation of the alpha-olefin propylene inhibits catalyst productivity; i.e., the rate at which the desired product aldehydes are formed. Specifically, the addition of small amounts of propyldiphenylphosphine or ethyldiphenylphosphine to rhodium hydroformylation solutions markedly reduced the rate of production of butyraldehydes from propylene, compared to the rate obtained in the absence of the alkyldiarylphosphines.

Although the presence of alkyldiarylphosphines in rhodium-catalyzed hydroformylation processes reduces the catalyst productivity, the stability of such rhodium complex catalysts can be enhanced by providing an alkyldiarylphosphine in the reaction medium and copending, commonly assigned U.S. application Ser. No. 762,335 filed Jan. 25, 1977 abandoned in favor of continuation U.S. Application Ser. No. 140,830, now U.S. Pat. No. 4,260,828. (Belgium Pat. No. 863,267), the entire disclosure of which is incorporated herein by reference thereto, teaches that the reaction conditions can be adjusted to be more severe in order to regain this apparent loss of catalyst productivity while retaining the enhanced catalyst stability.

Thus, it is known that, despite the obvious advantages of the above inventions, during use the rhodium complex catalyst loses activity (i.e. becomes partially deactivated) and eventually, after prolonged use, the activity of the catalyst will have decreased to such a point that it is no longer economically desirable to operate the hydroformylation process and the catalyst will have to be discharged and replaced with fresh catalyst. Accordingly, the discovery of new rhodium catalysts which may prove to be more robust than conventional rhodium-based catalysts in that they may be able to better withstand more severe reaction conditions and/or separation conditions that currently being practiced is of no small importance to the state of the art.

SUMMARY OF THE INVENTION

It has now been discovered that aldehydes can be prepared in good yields by employing certain heteronuclear-bridged rhodium clusters as the catalyst for such low pressure oxo hydroformylation reactions.

Thus, it is an object of this invention to provide novel heteronuclear-bridged rhodium clusters. It is another object of this invention to provide an improved process for preparing aldehydes by hydroformylating an olefin in the presence of a rhodium catalyst the improvement which comprises employing as the catalyst for said process, the heteronuclear-bridged rhodium clusters of this invention. Other objects and advantages from this invention will become readily apparent from the following description and appended claims.

Accordingly, a generic aspect of this invention relates to heteronuclear-bridged rhodium clusters having the generic formula

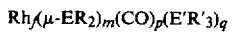

wherein E and E' each represent a Group VA element such as phosphorus, arsenic or antimony, and which may be the same or different; wherein R and R' each represent a monovalent organic radical composed of (1) carbon and hydrogen atoms or (2) carbon, hydrogen and aliphatic etheric oxygen atoms, each organic radical may be the same or different and are monovalently bonded to the Group VA element through a carbon atom or an aliphatic etheric oxygen atom thereof; wherein f has a value of from 2 to 6, m has a value of from 1 to 6, p has a value of from 1 to 6 and q has a value of from 1 to 6.

Another generic aspect of this invention can be described as an improved process for producing aldehydes by hydroformylation of an olefin with hydrogen and carbon monoxide in the presence of a rhodium catalyst the improvement comprising employing as the catalyst for said process a heteronuclear-bridged rhodium cluster having the generic formula

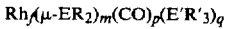

wherein E, E', R, R', f, m, p and q are the same as defined above.

DESCRIPTION OF THE PREFERRED EMBODIMENTS

As seen discussed above one of the basic points of novelty of this invention rests in the discovery of heteronuclear-bridged rhodium clusters having the generic formula

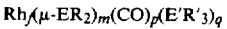

wherein E, E', R, R', i, m, p and q are the same as defined above and their use as catalysts for low pressure oxo hydroformylation reactions of an olefin to produce aldehydes.

As taught by P. Chini, in a review article entitled "The Closed Metal Carbonyl Clusters" published in Review (1968), *Inorganica Chimica* Acta, pages 31–51, states that a metal cluster compound is "a finite group of metal atoms which are held together entirely, mainly, or at least to a significant extent, by bonds directly between the metal atoms even though some non-metal atoms may be associated intimately with the cluster."

Accordingly, as seen by the above general empirical formula for the rhodium cluster compounds of this invention said clusters may contain (a) from 2 to 6 rhodium (Rh) atoms and more preferably contain 3 or 4 (f is preferably 3 or 4) rhodium atoms bonded to each other, (b) from 1 to 6, (preferably m is 3 or 4) diorgano Group VA element-bridging units ($\mu ER_2$), each linking two rhodium atoms, (c) from 1 to 6 (preferably p is 3 to 5) bridging and/or terminal carbonyl units, and (d) from 1 to 6 (preferably q is 1 or 2) triorgano Group VA element units (E'R'$_3$) bonded to rhodium.

While E and E' may be the same or different Group VA element such as phosphorus (P), arsenic (As) or antimony (Sb), preferably they are the same and most preferably phosphorus.

The organic radicals represented by R and R' may be the same or different and are composed of (1) carbon and hydrogen atoms or (2) carbon, hydrogen and aliphatic etheric oxygen atoms as explained above. The term "aliphatic etheric oxygen atom" as used herein is meant to convey the —O— group that bridges two hydrocarbon radicals such as e.g. in an ether radical or p-methoxyphenyl radical as well as the —O— group directly bonded to the Group VA element represented by E or E', such as e.g. in a diaryloxy phosphide or triarylphosphite unit, and to exclude the —O— group that forms part of a heterocyclic ring such as, e.g. dioxane. Moreover said organic radicals may contain other substituents, such as cyano and halo groups, e.g. chlorine which do not adversely affect the hydroformylation process discussed herein. Among the preferred organic radicals are hydrocarbon and hydrocarbonoxy groups containing from 1 to 20 carbon atoms such as alkyl, cycloalkyl, aryl, alkoxy and aryloxy radicals, the most preferred organic radicals being an alkyl or aryl radical, especially phenyl.

By way of illustration suitable diorgano Group VA element units ($\mu ER_2$) include the dialkoxyphosphides, the dialkoxyarsenides, the dialkoxystibides, the dialkylphosphides, the dialkylarsenides, the dialkylstibides, the dicycloalkylphosphides, the diaryloxyphosphides, the diaryloxyarsenides, the diaryloxystibides, the diarylphosphides, the diarylarsenides, the arylcycloalkylphosphides, the alkylarylphosphides, the alkylarylarsenides, the alkylarylstibides, the more preferred classes being the above mentioned phosphides, especially the dialkylphosphides and the diarylphosphides. Specific examples of such units include dimethoxyphosphide, diethoxyphosphide, di-n-propyloxyphosphide, di-n-butyloxyphosphide, di-2-ethylhexyloxyphosphide, di-n-octyloxyphosphide, di-n-dodecyloxyphosphide, diphenoxyphosphide, dimethylphosphide, diethylphosphide, di-n-propylphosphide, di-n-butylphosphide, di-2-ethylhexylphosphide, di-n-octylphosphide, di-n-dodecylphosphide, di-n-eicosylphosphide, diphenylphosphide, dinaphthylphosphide, di(p-chlorophenyl)phosphide, diphenylarsenide, diphenylstibide, di(p-methoxyphenyl)phosphide, di(p-cyanophenyl)phosphide, ethylphenylphosphide, and the like. The most preferred diorgano Group VA element unit is diphenylphosphide.

Illustrative suitable triorgano Group VA element units (E'R'$_3$) include the trialkylphosphites, the trialkylarsenites, the trialkylstibites, the triarylphosphites, the triarylarsenites, the triarylstibites, the triarylphosphines, the triarylarsines, the triarylstibines, the trialkylphosphines, the trialkylarsines, the trialkylstibines, the alkyldiarylphosphines, the dialkylarylphosphines and the tricycloalkylphosphines, the more preferred classes being the above mentioned phosphines and phosphites, especially the alkyldiarylphosphines and the triarylphosphines. Specific examples of such units include trimethylphosphite, triethylphosphite, butyldiethylphosphite, tri-n-propylphosphite, tri-n-butylphosphite, tri-2-ethylhexylphosphite, tri-n-octylphosphite, tri-n-dodecylphosphite, triphenylphosphite, trinaphthylphosphite, triphenylphosphine, tri(p-chlorophenyl)-phosphite, trinaphthylphosphine, phenyl diphenylphosphinite, diphenyl phenylphosphonite, diphenyl ethylphosphonite, triphenylarsine, triphenylstibine, tris(p-chlorophenyl)phosphine, tri(p-cyanophenyl)phosphite, tri(p-methoxyphenyl)phosphite, ethyl diphenylphosphinite, and the like. Triphenylphosphite and triphenylphosphine are examples of the most preferred units.

The most preferred heteronuclear-bridged rhodium clusters of this invention are bis(triphenylphosphine)-tricarbonyltris($\mu$-diphenylphosphido)trirhodium which may be illustrated by the empirical formula

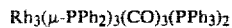

$Rh_3(\mu\text{-PPh}_2)_3(CO)_3(PPh_3)_2$ and triphenylphosphinepentacarbonyltetrakis($\mu$-diphenylphosphido)tetrarhodium which may be illustrated by the empirical formula

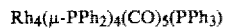

$Rh_4(\mu\text{-PPh}_2)_4(CO)_5(PPh_3)$ wherein Ph in the above two formulas represents a phenyl (i.e. $-C_6H_5$) radical.

The heteronuclear-bridged rhodium clusters of this invention can be prepared in a number of ways. In general it is preferred to build up the rhodium clusters of this invention from their corresponding tris(triorgano Group VA element) carbonylhydridorhodium complexes e.g.

$Rh(H)CO(E'R'_3)_3$ wherein E' and R' are the same as defined above. Such rhodium complexes as well as methods for their preparation are well known in the art. During the buildup of the rhodium clusters of this invention, some of the triorgano Group VA unit (E'R'$_3$) of the rhodium complex starting material is replaced with its corresponding diorgano Group VA unit ($\mu$-ER$_2$) which has a value (m) equal to the number of rhodium atoms (f) in the cluster and serves as a bridging group to help bind the cluster together. For instance, the rhodium three (Rh$_3$) clusters, e.g. $Rh_3(\mu\text{-PPh}_2)_3(CO)_3(PPh_3)_2$ can be prepared by heating its corresponding tris(triorgano Group VA element) carbonylhydridorhodium complex, e.g. $Rh(H)(CO)(PPh_3)_3$ wherein Ph is the same as defined above, while suspended in a solvent under an inert gas, preferably nitrogen until the desired rhodium cluster product solids precipitates out of solution. Likewise rhodium four clusters (Rh$_4$) may be prepared in the same manner except that a mixture of carbon monoxide and hydrogen gases (generally in about a 1:1 mole ratio) is employed to build up the carbonyl content in addition to the diorgano Group VA element ($\mu$-ER$_2$) content of the desired rhodium cluster, e.g. $Rh_4(PPh_2)_4(CO)_5(PPh_3)$. While any suitable temperature may be employed in said processes, in general temperatures within the range of about 80° to about 150° C. and more preferably from about 100° to about 130° C. should be useful in most instances. Moreover, while the reactions may be conducted under atmospheric pressure, in general pressures in the range of about 1 to about 1500 psig and preferably from about 50 to about 350 psig. are recommended. Although other inert gases may be employed in preparing Rh$_3$ clusters, the preferred inert gas is either argon or nitrogen. Suitable solvents or diluents which may be employed include hydrocarbons such as pentane, hexane, petroleum ether, heptane, octane, nonane, dodecane, 2-methylhexane, 2,2,3-trimethylpentane, cyclohexane, methylcyclohexane, benzene, toluene, ethylbenzene; ethers such as diethylether, di-n-butylether, tetrahydrofuran, dioxane, dimethoxyethane; ketones such as acetone, 2-butanone, cyclohexanone; aldehydes such as propionaldehyde, n-butyraldehyde, isobutyraldehyde, cyclohexanal; aldehyde condensation products such as Texanol ® (a mixture of butyraldehyde trimers); esters such as ethylacetate, n-butylacetate, ethylbutyrate; alcohols such as methanol, ethanol, iso-butanol; and diols such as 1,3-propylene glycol. Examples of the most preferred solvents are octane, nonane, benzene, toluene, tetrahydrofuran, acetone, and 2-butanone. Of course, the time of reaction will obviously be dependent upon the starting material and other conditions employed, however, completion of the reaction can be readily determined by routine techniques, such as infrared spectra.

In the same manner rhodium clusters containing more than four rhodium atoms can be prepared using the Rh$_3$ and/or Rh$_4$ type cluster products of this invention as the starting materials for such multiple rhodium clusters along with a suitable amount of tris(triorgano Group VA) carbonylhydridorhodium complex to satisfy the build-up of rhodium and diorgano Group VA content in the desired multiple rhodium cluster. Likewise any increase in carbonyl content of such desired multiple rhodium clusters may be provided for by the use of said mixture of carbon monoxide and hydrogen gases as explained above. The organo moieties and Group VA elements of the desired rhodium cluster will of course correspond to those moieties and elements present in the rhodium complex starting materials which may be varied as desired. The particular choice of operating conditions will merely be dependent upon the desired rhodium cluster to be produced and such conditions may be determined by routine experimentation.

The heteronuclear-bridged rhodium clusters of this invention are particularly useful as catalysts in the production of aldehydes via hydroformylation of an olefin. Said clusters have been found to be very robust and stable even under severe reaction conditions, e.g. reaction temperatures greater than 120° C., and thus may be employed under such conditions without experiencing the rapid loss of activity that is commonplace when the more reactive conventional rhodium complexes are employed under the same severe conditions. Thus it is believed that such rhodium clusters may eventually find more suitability than conventional rhodium complex catalysts in preparing aldehydes that require high operating temperatures such as those produced from internal olefins. In addition said rhodium clusters have already been found to catalyze the hydroformylation of $\alpha$-olefins to give aldehydes having a high normal to iso isomer ratio.

Accordingly another generic aspect of this invention comprises an improved process for producing aldehydes by hydroformylation of an olefin with hydrogen and carbon monoxide in the presence of a rhodium catalyst and at least 2 moles of free triorgano Group VA ligand per mole of the rhodium cluster, the improvement comprising employing as the catalyst for said process a heteronuclear-bridged rhodium cluster having the generic formula

$Rh_f(\mu\text{-ER}_2)_m(CO)_p(E'R'_3)_q$ wherein E, E', R, R', f, m, p and q are the same as defined above.

As pointed out by the above mentioned prior art, methods for hydroformylating olefins to produce aldehydes with a rhodium catalyst in the presence of free triorgano Group VA ligand are well known in the art. Thus it should be clear that the particular hydroformylation reactions encompassed by this invention, which can employ the novel rhodium clusters of this invention to catalyze said reaction, as well as the reaction conditions of such hydroformylation reactions are not critical features of this invention. The presently preferred hydroformylation processes are taught in U.S. Pat. No. 3,527,809 and U.S. Application Ser. Nos. 762,335 abandoned and 776,934, now U.S. Pat. No. 4,247,486.

Such hydroformylation processes involve producing aldehydes, preferably rich in their normal isomers, by reacting an olefin with hydrogen and carbon monoxide gas in a liquid reaction medium which contains the rhodium catalyst and at least 2 moles of free triorgano Group VA ligand per mole of the rhodium cluster and wherein the reaction conditions may consist essentially of (1) a temperature in the range of from about 50° to about 200° C., preferably from about 100° to about 150° C., (2) a total gas pressure of hydrogen, carbon monoxide and olefin of less than about 1500 psia., preferably less than about 400 psia. and more preferably less than about 350 psia.; (3) a carbon monoxide partial pressure of less than about 300 psia., preferably from about 1 to about 50 pisa.; and (4) a hydrogen partial pressure of less than 400 psia., preferably from about 20 to about 200 psia. Moreover, it is generally preferred that the ratio of hydrogen partial pressure to carbon monoxide partial pressure be greater than 2 to 1; while the amount of free triorgano Grup VA ligand present is preferably at least about 2 moles and more preferably at least about 10 moles per mole of rhodium cluster.

The heteronuclear-bridged rhodium clusters of this invention can be employed to catalyze the hydroformylation reaction in the same manner as taught in the prior art for any conventional catalyst. More preferably, however, the rhodium clusters of this invention are employed as the primary source of catalytic rhodium for the hydroformylation process. Preparation of the hydroformylation reaction medium using the rhodium clusters of this invention can be carried out in any manner since such is not a critical factor of the present invention. However, it is generally preferred to first prepare a diluted hydroformylation medium of said rhodium cluster compound and triorgano Group VA ligand, preferably along with a solvent for said rhodium cluster compound in the concentrations normally desired for a hydroformylation process. Such a dilution of the rhodium cluster with the triorgano Group VA ligand and a solvent to form such a hydroformylation medium can be carried out merely by mixing the ingredients involved in any suitable manner and in any order. However due to the sensitivity of the rhodium clusters to oxygen and/or water care should be taken to maintain said clusters under an inert atmosphere during the preparation of such hydroformylation mediums.

Of course it is obvious that the heteronuclear-bridged rhodium clusters of this invention can be employed individually or in the form of mixtures of two or more such cluster compounds as the catalyst for such hydroformylation reactions and the more preferred rhodium cluster compounds have already been disclosed above. Further, it is clear that the amount of rhodium cluster compound employed need only that minimum amount which is necessary to provide the desired rhodium concentration (which concentration in general may range from about 50 to about 500 ppm, preferably from about 100 to about 350 ppm of rhodium calculated as free metal) and which will furnish the basis for at least that catalytic amount of rhodium necessary to catalyze the particular hydroformylation process desired. Moreover, it is to be understood that while said rhodium cluster compounds are considered to be the catalyst of the hydroformylation reaction and are believed to maintain cluster integrity during the hydroformylation reaction it is possible that the empirical formula of such cluster compounds may undergo some change in their ligand configuration during the hydroformylation reaction. For example bis(triphenylphosphine)tricarbonyltris($\mu$-diphenylphosphido)trirhodium contains one vacant coordination site and may well pick up an addition carbonyl unit and/or other ligand during the hydroformylation reaction. Moreover, it is known in the art that some propyl diphenylphosphine is formed in situ during the continuous hydroformylation process of producing butyraldehyde in the presence of free triphenylphosphine and that such alkyldiarylphosphines have a greater affinity for rhodium than triarylphosphines. In any event the exact empirical formula of the rhodium cluster during hydroformylation is immaterial to this invention it being sufficient for the purpose of this invention to show that the heteronuclear-bridged rhodium clusters of this invention possess catalytic activity and can be employed to furnish said activity in such hydroformylation reactions.

The olefins that may be hydroformylated by the process of this invention as well as methods for their preparation are well known in the art and may contain from 2 to 20 carbon atoms. Said olefins are characterized by an internal or terminal ethylenic carbon to carbon bond, including alpha-olefins in which the terminal ethylenic group is a vinylidene group

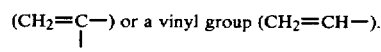

Said olefins may be straight chain or branched chain and may contain groups or substituents which do not essentially interfere with the course of the hydroformylation process, such as carbonyl

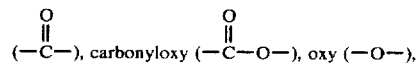

hydroxy(—OH), carboxy (—COOH), halo, alkoxy, phenyl, haloalkyl, and the like. Moreover said olefins may contain one or more ethylenic bonds.

Illustrative alpha olefinic compounds which can be employed as reactants include ethylene, propylene, 1-butene, 1-pentene, 1-hexene, 1-heptene, 1-octene, 1-decene, 1-dodecene, 1-octadecene, 2-ethyl-1-hexene, styrene, 3-phenyl-1-propene, 1,5-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, vinyl ethyl ether, vinyl methyl ether, allyl ethyl ether, n-propyl 7-octenoate, 3-butenoic acid, 7-octenoic acid, 3-butenenitrile, 5-hexenamide and the like. Illustrative internal olefinic compounds which can be employed as reactants include 2-pentene, 2-hexene, 3-hexene, 3-octene, 2-methyl-2-pentene, 3-hexen-1-ol, cyclohexene, and stilbene, and the like. Preferred alpha olefinic compounds include alkenes, alkyl alkenoates, alkenyl alkanoates, alkenyl alkyl ethers, and alkenols, especially those which contain from 2 to 20 carbon atoms.

As pointed out above another main ingredient present in the hydroformylation process of this invention is at least 2 moles of free triorgano Group VA ligand per mole of rhodium cluster i.e. ligand that is not tied or complexed with the rhodium atoms(s) in the rhodium cluster of this invention. Such free ligands are well known in the art and may be exemplified by the same ($E'R'_3$) formula given above for the triorgano Group VA element of the rhodium clusters of this invention wherein $E'$ and $R'$ are the same as described above. Accordingly said free triorgano Group VA ligand may correspond to any of the compounds already illustrated above for said triorgano Group VA formula ($E'R'_3$). However it is to be understood that, while it may be preferred to employ a free triorgano Group VA ligand that is the same as the triorgano Group VA element of the rhodium cluster in a given process, said ligand and said element need not be the same in a given process, but can be different if desired. The preferred free triorgano Group VA ligands are the triarylphosphines and triarylphosphites, especially triphenylphosphine. Moreover, preferred hydroformylation processes generally take place in the presence of at least 2 moles and more preferably at least 10 moles of free triorgano Group VA element per mole of rhodium cluster. As is well known the upper limit of the amount of free triorgano Group VA ligand is not particularly critical and is dictated primarily by commercial and economical considerations.

The hyroformylation process of this invention is also preferably conducted in the presence of a solvent for the heteronuclear-bridged rhodium clusters. Any suitable solvent for such clusters which does not essentially interfere with the hydroformylation process can be employed. Illustrative solvents that can be employed include heptane, octane, cyclohexane, benzene, toluene, xylenes, ethanol, n-butanol, 2-ethylhexanol, tetrahydrofuran, dimethoxyethane, 2-methoxyethylether, 2-methoxyethanol, tetraethyleneglycoldimethylether, ethyl acetate, 2-ethylhexanoate, propionaldehyde, n-butyraldehyde, iso-butyraldehyde, aldehyde condensation products like Texanol ® (a mixture of butyraldehyde trimers), acetone, 2-butanone, cyclohexanone, acetophenone, and the like. Illustrative examples of the preferred solvents are tetraethyleneglycoldimethylether, n-butyraldehyde, Texanol ®, cyclohexanone, and acetophenone.

Of course it is obvious that the amount of solvent employed is not critical to the subject invention and need only be that amount sufficient to provide the hydroformylation reaction medium with the particular rhodium concentration desired for said hydroformylation process. In general the amount of solvent when employed may range from about 5 percent by weight up to about 95 percent by weight or more based on the total weight of the hydroformylation reaction medium.

It is also generally preferred to carry out the hydroformylation process of this invention in a continuous manner. Such continuous hydroformylation processes are well known in the art and may involve the recycling of a rhodium catalyst-containing solution separated from the reaction product or the more preferred gas recycle technique described in U.S. application Ser. Nos. 762,335 and 776,934. Said gas recycle involves supplying to the liquid reaction medium a gaseous recycle stream containing at least hydrogen and unreacted olefin, and also supplying make-up quantities of carbon monoxide, hydrogen and olefin to said liquid reaction medium while removing from said liquid reaction medium a vapor phase mixture comprising unreacted olefin, hydrogen, vaporized aldehyde products and vaporized high boiling condensation products of said aldehydes, recovering said aldehyde and said aldehyde condensation products from said vapor phase mixure and forming said gaseous recycle steam, wherein the vaporized aldehyde condensation products are preferably removed from said liquid reaction medium in said vapor phase mixture at a rate which is substantially equal to the rate of their formation in said liquid reaction medium whereby the size of said liquid reaction medium is maintained substantially constant.

Of course, it is to be understood that the hydroformylation process of this invention can be carried out in the presence of addition materials, that are deliberately added to the hydroformylation reaction medium, if desired, for specific purposes or formed in situ during the hydroformylation process such as higher boiling liquid condensation products and alkyl substituted phosphines, and the like which have already been discussed above and are known in the art.

Moreover, it should be apparent that the amounts of the various individual components employed in the hydroformylation process of this invention are not narrowly critical to the operation of the present invention and that such general and preferred amounts have already been herein discussed above and can be readily found in the prior art.

Finally, the aldehyde products of the hydroformylation process of this invention have a wide range of utility that is well known and documented in the prior art e.g. they are especially useful as starting materials for the production of alcohols.

The following examples are illustrative of the present invention and are not to be regarded as limitative. It is to be understood that all of the parts, percentages and proportions referred to herein and in the appended claims are by weight unless otherwise indicated.

EXAMPLE 1

A 500 ml. glass pressure vessel equipped with a magnetic stirring bar was charged with 4.0 grams of tris(triphenylphosphine)carbonylhydridorhodium and 100 ml. of nonane. The vessel was sealed, attached to a gas manifold and purged two times with nitrogen by pressurizing to 60 psig, then venting to atmospheric pressure. A third and final charge of 60 psig. of nitrogen was left in the vessel and said vessel heated in a 125° C. oil bath for 16 hours. The vessel was then cooled to ambient temperature and vented. About 1.6 grams (75% yield) of a green solid rhodium cluster product were collected by filtration under nitrogen and dried under vacuum. Said rhodium product was identified by single-crystal x-ray crystallographic analysis [orthorhombic space group, Pna $2_1$: a=35.736(7) Angstroms; b=12.498(8) Angstroms; and c=14.484(5) Angstrom] to be bis(triphenylphosphine)tricarbonyltris($\mu$-diphenylphosphido)trirhodium and is also characterized by infrared bands at about 1985 and about 1945 cm$^{-1}$ (CH$_2$Cl$_2$ solution); a phosphorus-31 nuclear magnetic resonance spectrum which exhibits complex multiplets at about 52.0, 146.0, and 268.7 parts per million downfield from an external H$_3$PO$_4$ reference; and by elemental analysis:

Calculated for C$_{75}$H$_{60}$O$_3$P$_5$Rh$_3$: 61.16% C; 4.11%H; 10.51%P.

Found: 61.25%C; 4.41%H; 9.98%P.

Said rhodium cluster product can also be recrystallized from CH$_2$Cl$_2$/hexane, if desired.

EXAMPLE 2

A 500 ml. glass pressure vessel equipped with a magnetic stirring bar was charged with 0.93 grams of tris(triphenylphosphine)carbonylhydridorhodium and 50 ml. of nonane. The vessel was sealed, attached to a gas manifold and purged two times with carbon monoxide/hydrogen gas (CO/H$_2$, 1:1 mole ratio) by pressurizing to 60 psig., then venting to atmospheric pressure. A third and final charge of 60 psig. of CO/H$_2$ gas (1:1 mole ratio) was left in the vessel and said vessel heated in a 130° C. oil bath for 15 hours. The vessel was then cooled to ambient temperature and vented. About 0.11 grams (30% yield) of a brown solid rhodium cluster product were collected by filtration under argon and dried under vacuum. Said rhodium product was identified by single-crystal x-ray crystallographic analysis [monoclinic space group, P2$_1$/c: a=17.586(7) Angstroms; b=14.438(9) Angstroms; c=25.259(8) Angstroms and beta (angle) =97.08 (3) degrees] to be triphenylphosphinepentacarbonyltetrakis($\mu$-diphenylphosphido)tetrarhodium and also is characterized by infrared bands at about 1980, 1840 and 1800 cm$^{-1}$; and by elemental analysis: calculated for C$_{71}$H$_{55}$O$_5$P$_5$Rh$_4$: 54.85%C; 3.57%H; Found: 53.77%C; 3.82%H.

EXAMPLE 3

A 500 ml. glass pressure vessel equipped with a magnetic stirring bar was charged with 0.15 grams of carbonyltriphenylphosphine-acetylacetonatorhodium, 5.0 grams of triphenylphosphine and 95 grams of Texanol ®, a mixture of butyraldehyde trimers. The vessel was then sealed, attached to a gas manifold and purged four times with carbon monoxide/hydrogen gas (CO/H$_2$, 1:1 mole ratio) by pressurizing to 60 psig., then venting to atmospheric pressure. A fifth and final charge of 60 psig. of CO/H$_2$ gas (1:1 mole ratio) was left in the vessel and the vessel heated in a 100° C. oil bath for 44 hours. The dark brown reaction solution product was then cooled to ambient temperature, transferred to a flask and stored under argon. Said reaction solution product was then analyzed and the only rhodium-containing species detected in said solution were triphenylphosphinepentacarbonyltetrakis($\mu$-diphenylphosphido)tetrarhodium (in a major amount) along with a small amount of bis(triphenylphosphine)-tricarbonyltris($\mu$-diphenylphosphido)trirhodium.

EXAMPLE 4

A 500 ml. glass pressure vessel equipped with a magnetic stirring bar was charged with a 0.3 grams of tris(triphenylphosphine)carbonylhydridorhodium, 20 grams of triphenylphosphine, and 192 ml. of tetraethyleneglycoldimethylether. The vessel was then sealed, attached to a gas manifold and purged four times with carbon monoxide/hydrogen gas (CO/H$_2$), 1:1 mole ratio) by pressurizing to 80 psig., then venting to atmospheric pressure. A fifth and final charge of 80 psig. of CO/H$_2$ gas (1:1 mole ratio) was left in the vessel and the vessel heated in a 100° C. oil bath for 66 hours. The dark brown reaction solution was then cooled to ambient temperature, transferred to a flask and stored under argon. Said reaction solution was then analyzed and the only rhodium-containing species detected in said solution were triphenylphosphinepentacarbonyltetrakis($\mu$-diphenylphosphido)tetrarhodium (in a major amount) along with a small amount of bis(triphenylphosphine)tricarbonyltris($\mu$-diphenylphosphido)trirhodium.

EXAMPLE 5

To a 300 ml. stirred autoclave were charged 40 ml. of the rhodium cluster product solution prepared as described in Example 3 and 10 ml. of 1-pentene. The autoclave was then purged three times with carbon monoxide/hydrogen gas (CO/H$_2$), 1:1 mole ratio) by pressurizing to 200 psig., then venting to atmospheric pressure. A fourth and final charge of 200 psig. of CO/H$_2$ gas (1:1 mole ratio) was left in the autoclave and the autoclave heated to 150° C. A rapid pressure drop was observed. The reaction temperature was maintained at 150° C. for 1.5 hours and then lowered to ambient temperature. Analysis of the hydroformylation reaction product solution shown that about 75% of the 1-pentene had been converted to its corresponding aldehydes (i.e. a mixture of 1-hexanal and 2-methylpentanal) which has a normal-/iso isomer ratio of 5 to 1, and that 25% of the 1-pentene had isomerized to 2-pentene.

Similarly 50 ml. of a solution of the rhodium cluster product prepared by the method described in Example 3, 10 ml. of 1-pentene, and 96 ml. of 2-methoxyethylether were hydroformylated under 500 psig. of CO/H$_2$ gas (1:1 mole ratio) at both 135° C. and 130° C. for 1.5 hours. Analysis of the resulting aldehyde product mixture for said process conducted at 135° C. showed about 100% conversion of the 1-pentene to its aldehydes, that the aldehyde product mixture had a normal/iso isomer ratio of 5.1 to 1; and that only a trace of the 1-pentene had isomerized and that only a trace of the 1-pentene was unreacted. Analysis of the resulting product mixture for said process conducted at 130° C. showed 96% conversion of the 1-pentene to its aldehydes, that the aldehyde product mixture had a normal-/iso isomer ratio of 3.6 to 1; that 4% of the 1-pentene was unreacted and that only a trace of the 1-pentene had isomerized.

EXAMPLE 6

The procedure of Example 5 was repeated using 500 psig. of CO/H$_2$ gas (1:1 mole ratio) and a hydroformylation reaction temperature of 135° C. Analysis of the hydroformylation reaction product solution showed that about 86% of the 1-pentene had been converted to its corresponding aldehydes (i.e. a mixture of 1-hexanal and 2-methylpentanal) which had a normal/iso isomer ratio of 3.9 to 1; and that about 14% of the 1-pentene had isomerized to 2-pentene.

EXAMPLE 7

The procedure in Example 3 was repeated using 0.3 grams of carbonyltriphenylphosphineacetylacetonatorhodium, 20 grams of triphenylphosphine and 96 ml of 2-methoxyethylether and heating the vessel in a 100° C. oil bath for 25 hours under 60 psig. of CO/H$_2$ gas (1:1 mole ratio). The dark brown reaction solution product was analyzed and the only rhodium-containing species detected in said solution were triphenylphosphinepentacarbonyltetrakis($\mu$-diphenylphosphido)tetrarhodium (in a major amount) along with a small amount of bis(triphenylphosphine)tricarbonyltris($\mu$-diphenylphosphido)trirhodium.

EXAMPLE 8

To a 300 ml. stirred autoclave were charged 50 ml. of the rhodium cluster product solution prepared as described in Example 7 and 10 ml. of cis-2-pentene. The autoclave was then purged three times with carbon monoxide/hydrogen gas ($CO/H_2$, 1:1 mole ratio) by pressurizing to 500 psig., then venting to atmospheric pressure. A fourth and final charge of 200 psig. of $CO/H_2$ gas (1:1 mole ratio) was left in the autoclave. The autoclave was heated for 1.5 hours at 130° C. and then cooled to ambient temperature. Analysis of the hydroformylation reaction product solution showed that about 91% of the cis-2-pentene had been converted to its corresponding aldehydes (i.e. a mixture of 2-methylpentanal and 2-ethylbutyraldehyde).

EXAMPLE 9

The procedure in Example 8 was repeated except that 10 ml. of vinylethylether were used instead of cis-2-pentene. Analysis of the hydroformylation reaction product solution showed that about 95% of the vinylethylether had been converted to its corresponding aldehydes (i.e. a mixture of 3-ethoxypropionaldehyde and 2-ethoxypropionaldehyde) which had a normal/iso isomer ratio of 1.7 to 1, and that about 5% of the vinylethylether was unreacted.

EXAMPLE 10

The procedure in Example 8 was repeated except that 10 ml. of acroleindiethylacetal were used instead of cis-2-pentene. Analysis of the hydroformylation reaction product solution showed that essentially 100% of the acroleimdiethylacetal had been converted to its corresponding aldehydes (i.e. a mixture of 4,4-diethoxybutyraldehyde and 2-methyl-3,3-diethoxypropionaldehyde) which had a normal/iso isomer ratio of 1.5 to 1.

EXAMPLE 11

Ten ml. of 1-hexene and 50 ml. of a solution consisting of 0.15 grams of a bis(triphenylphosphine)tricarbonyltris($\mu$-diphenylphosphido)trirhodium (prepared by the method described in Example 1), 5.0 grams of triphenylphosphine and 95 ml. of tetraethyleneglycoldimethylether were charged to a 300 ml. stirred autoclave and purged two times with nitrogen by pressurizing to 100 psig., then venting to atmospheric pressure. The autoclave was pressurized with 100 psig. nitrogen a third time, then vented to 5 psig. After the temperature of the autoclave was brought to 100° C., 50 psig. $CO/H_2$ gas (1:1 mole ratio) was added (total gas pressure approximately 100 psig.) and gas consumption began. Each time the pressure dropped by 5 psig., $CO/H_2$ gas (1:1 mole ratio) was added to bring the total gas pressure back to 100 psig. After approximately 25 minutes, gas consumption had nearly stopped and the autoclave was cooled to ambient temperature. Analysis of the hydroformylation reaction solution showed that about 57% of the 1-hexene had been converted to aldehydes (i.e. 1-heptanal and 2-methylhexanal), 42% of the 1-hexene had isomerized, while about 1% of the 1-hexene remained unreacted.

EXAMPLE 12

The procedure in Example 11 was repeated except that 5.0 grams of triphenylantimony was employed rather than 5.0 grams of triphenylphosphine. Analysis of the hydroformylation product solution showed that about 20% of the 1-hexene had been converted to its corresponding aldehydes and that the product mixture had a normal isomer ratio of 5 to 1, while 80% of the 1-hexene had isomerized into 2-hexene.

EXAMPLE 13

The procedure in Example 11 was repeated except that 3.0 ml. of triethylphosphine was used in place of 5.0 grams of triphenylphosphine. Analysis of the hydroformylation product solution showed that about 59% of the 1-hexene had been converted to its corresponding aldehydes and that the product mixture had a normal/iso isomer ratio of 2.9 to 1, and that 9% of the 1-hexene had isomerized into 2-hexene while about 32% of the 1-hexene remained unreacted.

EXAMPLE 14

The procedure in Example 11 was repeated using a solution consisting of 0.12 grams of triphenylphosphine pentacarbonyltetrakis($\mu$-diphenylphosphido)tetrarhodium (prepared by the method described in Example 2), 2.7 ml. of n-propyldiphenylphosphine, 10.0 ml. of 1-hexene and 89.9 ml. of tetraethyleneglycoldimethylether. Analysis of the hydroformylation product solution showed that about 81% of the 1-hexene had been converted to its corresponding aldehydes and that the aldehyde product mixture had a normal/iso isomer ratio of 7.0 to 1.

EXAMPLE 15

The procedure in Example 11 was repeated using a 60 ml. solution derived from a solution consisting of 0.10 grams of a triphenylphosphinepentacarbonyltetrakis($\mu$-diphenylphosphido)tetrarhodium (prepared by the method described in Example 2), 6.7 grams of triphenylphosphine, 22 ml. of 1-pentene and 147.8 ml. of tetraethyleneglycoldimethylether. Analysis of the resulting hydroformylation product solution showed that about 84% of the 1-pentene had been converted to its corresponding aldehydes (i.e. a mixture of 1-hexanal and 2-methylpentanal) and that the aldehyde product mixture had a normal/iso isomer ratio of 4.8 to 1.

EXAMPLE 16

Twenty ml. of a solution derived from a solution consisting of 0.11 grams of triphenylphosphinepentacarbonyltetrakis($\mu$-diphenylphosphido)tetrarhodium, 7.45 grams of triphenylphosphine and 120 ml. of tetraethyleneglycoldimethylether was charged to a modified glass pressure vessel so that the continuous hydroformylation of propylene could be studied. The reaction medium was heated to 105° C. under a continuous gas pressure of about 180 psig. (27 psig. $H_2$ gas, 25 psig. CO gas and 60 psig. propylene, the remainder being $N_2$ gas) for six days. Analysis of the off-gases over the six days indicated a constant reaction rate and a constant butyraldehyde normal/iso isomer ratio of 4.6 to 1.

EXAMPLE 17

On the sixth day of the continuous hydroformylation process of Example 16, the composition of the gas reactants was changed to about 90 psig. $H_2$ gas, 14 psig. CO gas and 40 psig. of propylene and the hydroformylation continued for 13 days. Analysis of the off-gases over said 13 days of continuous hydroformylation showed that the butyraldehyde product mixture had an average normal/iso isomer ratio of 9.6 to 1.

Various modifications and variations of this invention will be obvious to a worker skilled in the art and it is to be understood that such modifications and variations are to be included within the purview of this application and the spirit and scope of the appended claims.

What is claimed is:

1. In a hydroformylation process for producing aldehydes by hydroformylating an olefin with hydrogen and carbon monoxide in the presence of a hydroformylation reaction medium comprising a soluble rhodium complex catalyst, a solvent for said catalyst, and at least 2 moles of a free triorgano Group VA element ligand, wherein the reaction conditions consist essentially of (1) a temperature in the range of from about 50° to about 200° C., (2) a total gas pressure of hydrogen, carbon monoxide and olefin of less than about 1500 psia., (3) a carbon monoxide partial pressure of less than about 300 psia. and (4) a hydrogen partial pressure of less than 400 psia., the improvement comprising employing as the catalyst for said process a catalytic amount of a heteronuclear-bridged rhodium cluster compound having the generic formula $$Rh_f(\mu\text{-}ER_2)_m(CO)_p(E'R'_3)_q$$

wherein E and E' each individually represent a Group VA element selected from the group consisting of phosphorus, arsenic or antimony; wherein R and R' each individually represent a monovalent organic radical selected from the group consisting of alkyl, aryl, alkoxy and aryloxy radicals; wherein f has a value of from 2 to 6, m has a value of from 1 to 6, p has a value of from 1 to 6 and q has a value of from 1 to 6.

2. A process as defined in claim 1, wherein E and E' each represent a phosphorus atom.

3. A process as defined in claim 2, wherein f has a value of 3 to 4; m has a value of 3 to 4; p has a value of 3 to 5 and q has a value of 1 to 2.

4. A process as defined in claim 2, wherein R and R' are selected from the group consisting of alkyl and aryl radicals.

5. A process as defined in claim 4, wherein R and R' each represent a phenyl radical.

6. A process as defined in claim 3, wherein R and R' are selected from the group consisting of alkyl and aryl radicals.

7. A process as defined in claim 6, wherein R and R' each represent a phenyl radical.

8. A process as defined in claim 7, wherein f is 3; m is 3; p is 3 and q is 2.

9. A process as defined in claim 7, wherein f is 4; m is 4; p is 5 and q is 1.

10. A process as defined in claim 1, wherein the free triorgano Group VA ligand is triphenylphosphine and wherein the process is conducted in a continuous manner.

11. A process as defined in claim 7, wherein the free triorgano Group VA ligand is triphenylphosphine and wherein the process is conducted in a continuous manner.

* * * * *